United States Patent [19]

Sugavanam et al.

[11] Patent Number: 5,204,363
[45] Date of Patent: * Apr. 20, 1993

[54] HETEROCYCLIC COMPOUNDS

[75] Inventors: Balasubramanyan Sugavanam; Paul A. Worthington, both of Berkshire; John M. Clough, Buckinghamshire, all of England

[73] Assignee: Imperial Chemical Industries PLC, London, England

[*] Notice: The portion of the term of this patent subsequent to Apr. 2, 2008 has been disclaimed.

[21] Appl. No.: 642,835

[22] Filed: Jan. 18, 1991

Related U.S. Application Data

[63] Continuation of Ser. No. 298,835, Jan. 18, 1989, Pat. No. 5,004,494, which is a continuation of Ser. No. 007,352, Jan. 27, 1987, abandoned, which is a continuation of Ser. No. 353,941, Mar. 2, 1982, abandoned.

Foreign Application Priority Data

| Mar. 18, 1981 [GB] United Kingdom | 8108412 |
| Oct. 16, 1981 [GB] United Kingdom | 8131301 |
| Oct. 29, 1981 [GB] United Kingdom | 8132682 |

[51] Int. Cl.$^5$ ............... A01N 43/653; C07D 249/08
[52] U.S. Cl. ........................... 514/383; 514/184; 548/101; 548/268.6
[58] Field of Search ............... 514/184, 383; 548/101, 548/268.6

[56] References Cited

U.S. PATENT DOCUMENTS

| 4,079,143 | 3/1978 | Balasubramenyan et al. | 548/268.6 |
| 5,004,494 | 4/1991 | Sugavanan et al. | 548/268.6 |

*Primary Examiner*—Patricia L. Morris
*Attorney, Agent, or Firm*—Cushman, Darby & Cushman

[57] ABSTRACT

Triazole and imidazole compounds having the general formula (I):

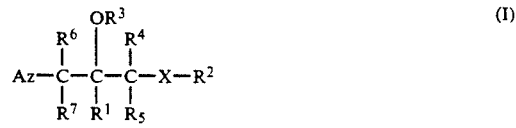

wherein $R^1$ and $R^2$, which may be the same or different, are hydrogen, alkyl, optionally substituted cycloalkyl, cycloalkylmethyl, alkenyl, heterocyclyl, aryl or aralkyl optionally substituted with halogen, nitro alkyl, haloalkyl, haloalkoxy, alkoxy, phenyl, phenoxy, benzyl, benzylosy, halophenyl or haloalkoxy; $R^3$ is hydrogen, alkyl, alkenyl, alkynyl, aralkyl or acyl; $R^4$ and $R^5$, which may be the same or different, are hydrogen, alkyl, alkenyl or optionally substituted aryl; $R^6$ and $R^7$, which may be the same or different, are hydrogen, alkyl, alkenyl or optionally substituted aryl; X is oxygen or sulphur or is SO or $SO_2$; and Az is 1,2,4- or 1,3,4-triazole or imidiazole ring; and isomers, acid addition salts and metal complexes thereof. The compounds are useful as plant fungicides.

2 Claims, No Drawings

HETEROCYCLIC COMPOUNDS

This is a continuation of application Ser. No. 07/298,835, filed Jan. 18, 1989, now U.S. Pat. No. 5,004,494, issued Apr. 2, 1991 which is a continuation of Ser. No. 07/007,352, filed Jan. 27, 1987, now abandoned, which is a continuation of Ser. No. 353,941, filed Mar. 2, 1982, now abandoned.

This invention relates to triazole and imidazole compounds useful as fungicides, to a process for preparing them, to fungicidal compositions containing them, and to a method of combating fungal infections in plants using them.

The triazole and imidazole compounds have the general formula (I):

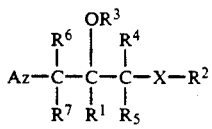

wherein $R^1$ and $R^2$, which may be the same or different, are hydrogen, alkyl, optionally substituted cycloalkyl, cycloalkylmethyl, alkenyl, heterocyclyl, aryl or aralkyl optionally substituted with halogen, nitro, alkyl, haloalkyl, alkoxy, phenyl, phenoxy, benzyl, benzyloxy, halophenyl or haloalkoxy; $R^3$ is hydrogen, alkyl, alkenyl, alkynyl, aralkyl or acyl; $R^4$ and $R^5$, which may be the same or different, are hydrogen, alkyl, alkenyl or optionally substituted aryl; $R^6$ and $R^7$, which may be the same or different, are hydrogen, alkyl, alkenyl or optionally substituted aryl; X is oxygen or sulphur or is SO or $SO_2$ and Az is a 1,2,4- or 1,3,4-triazole or imidazole ring; and isomers, acid addition salts and metal complexes thereof.

The compounds of the invention contain at least one chiral centre. Such compounds are generally obtained in the form of isomeric mixtures. However, these and other mixtures can be separated into the individual isomers by methods known in the art.

The alkyl groups may be straight or branched chain groups having 1 to 6, e.g. 1 to 4, carbon atoms; examples are methyl, ethyl, propyl (n- or iso-propyl) and butyl (n-, sec-, iso- or t-butyl). Cycloalkyl groups may be, for example, cyclopropyl, cyclopentyl or cyclohexyl.

Examples of suitable substituents for the aryl and aralkyl groups, which are preferably optionally substituted phenyl and benzyl, are halogen (e.g. fluorine, chlorine or bromine), $C_{1-5}$ alkyl [e.g. methyl, ethyl, propyl (n- or iso-propyl) and butyl (n-, sec-, iso-or t-butyl], $C_{1-4}$ alkoxy (e.g. methoxy and ethoxy), halo-$C_{1-4}$ alkyl (e.g. trifluoromethyl or 1,1,2,2-tetrafluoroethyl), halo-$C_{1-4}$ alkoxy (e.g. trifluoromethoxy or 1,1,2,2-tetrafluoroethoxy), nitro, cyano, phenyl, phenoxy, benzyl, benzyloxy (any of the latter four groups may be ring substituted, e.g. with halogen), alkylenedioxy, haloalkylenedioxy (e.g. difluoromethylenedioxy), amino, acetylamino, mono- or di- $C_{1-4}$ alkylamino (e.g. dimethylamino), hydroxy, morpholino and carboxy (and alkyl esters thereof).

The alkyl moiety of a benzyl group can be substituted with, for example, one or two alkyl groups (e.g. methyl or ethyl). When substituted the phenyl and benzyl groups may bear one, two or three substituents as defined above.

Preferably the phenyl and benzyl groups have a substituent in the 2-, 3- or 4- position. Examples of these groups are phenyl, benzyl, α-methylbenzyl, 2-, 3- or 4-chlorophenyl, 2,4- or 2,6-dichlorophenyl, 2-, 3- or 4-fluorophenyl, 2,4-or 2,6-difluorophenyl, 2-, 3- or 4bromophenyl, 2-chloro-4-fluorophenyl, 2-fluoro-4-chlorophenyl, 2-chloro-6-fluorophenyl, 2-, 3- or 4-methoxyphenyl, 2,4-dimethoxyphenyl, 2-, 3- or 4-ethoxyphenyl, 2-, 3- or 4-nitrophenyl, 2-chloro-4-nitrophenyl, 2-chloro-5-nitrophenyl, 2-, 3- or 4-methylphenyl, 2,4-dimethylphenyl, 2-, 3- or 4-t-butylphenyl, 2-, 3- or 4-trifluoromethylphenyl, 2-, 3- or 4-trifluoromethoxyphenyl, 2-, 3- or 4-(1,1,2,2-tetrafluoroethyl)phenyl, 2,3-(difluoromethylenedioxy)phenyl, 2-fluoro-4-methoxyphenyl, 2-methoxy-4-fluorophenyl, 2-methoxy-4-chlorophenyl, 2-methoxy-4-fluorophenyl, 2-, 3- or 4-phenoxyphenyl, 2-, 3- or 4-phenylphenyl (2-, 3- or 4-biphenyl), 2-, 3- or 4-benzylphenyl, 2-, 3- or 4-benzyloxyphenyl, 2-, 3- or 4-(4-chloro- or 4-fluorobenzyloxy)phenyl, 2-, 3- or 4-aminophenyl, 2-, 3- or 4-(N,N-dimethylamino)phenyl, 2-, 3- or 4-hydroxyphenyl, 2-, 3- or 4-carboxyphenyl, 2-, 3- or 4-(methoxycarbonyl)phenyl, 2-, 3- or 4-morpholinophenyl and the corresponding ring substituted benzyl and -methyl benzyl groups.

Heterocyclic groups may be, for example, pyridyl, furyl or thienyl.

In a further aspect the invention provides the triazole and imidazole compounds having the general formula (I):

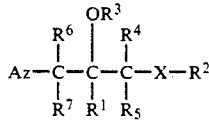

wherein $R^1$ is hydrogen, alkyl, optionally substituted cycloalkyl, cycloalkylmethyl, alkenyl, heterocyclyl, aryl or aralkyl optionally substituted with halogen, nitro, alkyl, haloalkyl, alkoxy, haloalkoxy, phenyl, phenoxy, benzyl, benzyloxy, halophenyl, haloalkoxy; $R^2$ is any of the values for $R^1$ except optionally substituted phenyl when X is oxygen and $R^3$ to $R^7$ are hydrogen; $R^3$ is hydrogen, alkyl, alkenyl, alkynyl, aralkyl or acyl; $R^4$ and $R^5$, which may be the same or different, are hydrogen, alkyl, alkenyl or optionally substituted aryl; $R^6$ and $R^7$, which may be the same or different, are hydrogen, alkyl, alkenyl or optionally substituted aryl; X is oxygen or sulphur or is SO or $SO_2$ and Az is a 1,2,4- or 1,3,4-triazole or imidazole ring; and isomers, acid addition salts and metal complexes thereof.

In another aspect the invention provides triazole and imidazole compounds having the general formula (I):

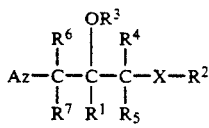

wherein $R^1$ and $R^2$, which may be the same or different, are alkyl, cycloalkyl, phenyl or benzyl optionally substituted with halogen, alkyl, alkoxy, phenyl, halophenyl, $R^3$ is hydrogen or $C_{1-6}$ alkyl; $R^4$ and $R^5$, which may be the same or different are hydrogen, $C_{1-6}$ alkyl or allyl; $R^6$ and $R^7$ are hydrogen; X is oxygen and Az is a 1,2,4- triazole ring; and acid addition salts and metal complexes thereof.

The invention further includes compounds as defined in the preceding paragraph but wherein $R^2$ is other than optionally substituted phenyl when X is oxygen and $R^3$ to $R^7$ are hydrogen.

In a still further aspect the invention provides triazole and imidazole derivatives as claimed in the claim 1 wherein in formula I $R^1$ is $C_{1-6}$ alkyl, phenyl or halophenyl; $R^2$ is $C_{1-6}$ alkyl, cycloalkyl or phenyl, both of which may be substituted with alkyl, alkoxy, phenyl, halogen or halophenyl; $R^3$ is hydrogen or $C_{1-6}$ alkyl; $R^4$, $R^5$, $R^6$ and $R^7$ are hydrogen or $C_{1-6}$ alkyl; and X is oxygen.

In a yet further aspect the invention provides triazole and imidazole derivatives as defined in the preceding paragraphs wherein $R^2$ is other than optionally substituted phenyl when Az is a 1,2,4-triazole or imidazole ring, X is O, $R^1$ is alkyl, optionally substituted phenyl or optionally substituted cycloalkyl and $R^3$, $R^4$, $R^5$, $R^6$ and $R^7$ are hydrogen.

The salts can be salts with inorganic or organic acids e.g. hydrochloric, nitric, sulphuric, acetic, 4-toluene sulphonic or oxalic acid.

Suitably the metal complex is one including, as the metal, copper, zinc, manganese or iron. It preferably has the general formula:

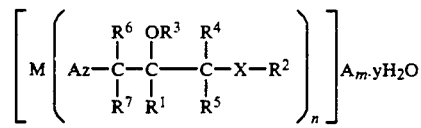

wherein $R^1$, $R^2$, $R^3$, $R^4$, $R^5$, $R^6$ and $R^7$, Az and X are as defined above, M is metal, A is an anion (e.g. a chloride, bromide, iodide, nitrate, sulphate or phosphate anion), n is 2 or 4 and y is 0 or an integer of 1 to 12, and m is an integer consistent with valency.

Examples of the compounds of the invention are shown in Table I below. These compounds correspond to the general formula:

TABLE I

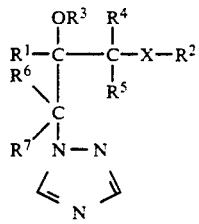

| COMPOUND NO | $R^1$ | $R^2$ | $R^3$ | $R^4$ | $R^5$ | $R^6$ | $R^7$ | X | Melting Point °C. |
|---|---|---|---|---|---|---|---|---|---|
| 1 | t-butyl | 4-chlorophenyl | H | H | H | H | H | O | 85.5–87 |
| 2 | t-butyl | 4-phenylphenyl | H | H | H | H | H | O | 120.5–122 |
| 3 | t-butyl | 4-chlorophenyl-phenyl | H | H | H | H | H | O | |
| 4 | t-butyl | 2,4-dichlorophenyl-phenyl | H | H | H | H | H | O | 126–127 |
| 5 | t-butyl | i-propyl | H | H | H | H | H | O | |
| 6 | t-butyl | n-propyl | H | H | H | H | H | O | |
| 7 | t-butyl | 4-fluorophenyl | CH$_3$ | H | H | H | H | O | Oil |
| 8 | t-butyl | 4-chlorophenyl | H | H | H | H | H | O | |
| 9 | 4-chlorophenyl | i-propyl | H | H | H | H | H | O | |
| 10 | 4-chlorophenyl | 4-chlorophenyl | H | H | H | H | H | O | 93–94.5 |
| 11 | 4-chlorophenyl | 2,4-dichloro-phenyl | H | H | H | H | H | O | |
| 12* | t-butyl | 4-chlorophenyl | H | H | H | H | H | O | 160–161 |
| 13 | t-butyl | 4-fluorophenyl | H | H | H | H | H | O | 76–77 |
| 14 | 4-chlorophenyl | methyl | H | H | H | H | H | O | 95–96 |
| 15 | t-butyl | 2-chloro-4-methoxyphenyl | H | H | H | H | H | O | 108–109 |

*Compound No. 12 is an imidazole derivative, i.e. the triazole ring in the formula is an imidazole ring, thus

| 16 | phenyl | 4-methoxyphenyl | H | H | H | H | H | S | Gum |
| 17 | 4-chlorophenyl | 4-fluorophenyl | H | H | H | H | H | S | 83–85 |
| 18 | 2-chlorophenyl | 4-fluorophenyl | H | H | H | H | H | S | Gum |
| 19 | 2-fluorophenyl | 4-fluorophenyl | H | H | H | H | H | S | 80–82 |
| 20 | 2-fluorophenyl | 4-chlorophenyl | H | H | H | H | H | S | 70–72 |
| 21 | 2-chlorophenyl | 4-chlorophenyl | H | H | H | H | H | S | Gum |
| 22 | t-butyl | 4-chlorophenyl | H | H | H | H | H | S | 64–65 |
| 23 | phenyl | 4-methoxyphenyl | H | H | H | H | H | SO | 190–195* |
| 24 | 2-fluorophenyl | 4-fluorophenyl | H | H | H | H | H | SO | Gum* |
| 25 | 2-fluorophenyl | 4-chlorophenyl | H | H | H | H | H | SO* | 130–136 (decomposition) |
| 26 | t-butyl | 4-chlorophenyl | H | H | H | H | H | SO* | 140–145 (decomposition) |
| 27 | phenyl | 4-methoxyphenyl | H | H | H | H | H | SO$_2$ | Glass |
| 28 | 4-chlorophenyl | 4-fluorophenyl | H | H | H | H | H | SO$_2$ | 124–125 (decomposition) |
| 29 | 2-fluorophenyl | 4-fluorophenyl | H | H | H | H | H | SO$_2$ | 104–105 |

TABLE I-continued

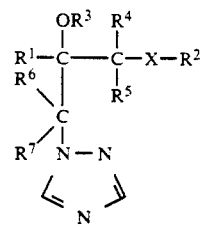

| COMPOUND NO | R¹ | R² | R³ | R⁴ | R⁵ | R⁶ | R⁷ | X | Melting Point °C. |
|---|---|---|---|---|---|---|---|---|---|
| 30 | 2-fluorophenyl | 4-chlorophenyl | H | H | H | H | H | SO$_2$ | (decomposition) 102-104 |
| 31 | t-butyl | 4-chlorophenyl | H | H | H | H | H | SO$_2$ | (decomposition) 114-116 |
| 32 | 4-chlorophenyl | methyl | H | CH$_3$ | CH$_3$ | H | H | O | 103-104.5 |

*Mixture of diastereoisomers

| | | | | | | | | | |
|---|---|---|---|---|---|---|---|---|---|
| 33 | t-butyl | 2-chloro-4-phenylphenyl | H | H | H | H | H | O | 83-84 |
| 34 | 2,4-dichlorophenyl | methyl | H | H | H | H | H | O | 105-106 |
| 35 | 4-fluorophenyl | methyl | H | H | H | H | H | O | 89.5-91 |
| 36 | t-butyl | 4-methylphenyl | H | H | H | H | H | O | 105-106 |
| 37 | 2-fluorophenyl | 4-phenylphenyl | H | H | H | H | H | O | 138-139 |
| 38 | t-butyl | 4-methoxyphenyl | H | H | H | H | H | O | 78-79 |
| 39 | i-propyl | 4-phenylphenyl | H | H | H | H | H | O | 137-138.5 |
| 40 | t-butyl | 2-phenylphenyl | H | H | H | H | H | O | 106-107 |
| 41 | phenyl | i-propyl | H | H | H | H | H | O | |
| 42 | 4-chlorophenyl | i-propyl | H | H | H | H | H | O | Oil |
| 43 | 4-fluorophenyl | i-propyl | H | H | H | H | H | O | Oil |
| 44 | 2,4-dichlorophenyl | i-propyl | H | H | H | H | H | O | Oil |
| 45 | 4-fluorophenyl | i-propyl | H | H | H | H | H | O | 121-122* (decomposes) |
| 46 | 4-chlorophenyl | i-propyl | H | CH$_3$ | CH$_3$ | H | H | O | |
| 47 | 4-fluorophenyl | i-propyl | H | CH$_3$ | CH$_3$ | H | H | O | |
| 48 | 2,4-dichlorophenyl | i-propyl | H | CH$_3$ | CH$_3$ | H | H | O | |
| 49 | phenyl | -n-propyl | H | H | H | H | H | O | |
| 50 | 4-chlorophenyl | -n-propyl | H | H | H | H | H | O | Oil |
| 51 | 4-fluorophenyl | -n-propyl | H | H | H | H | H | O | Oil |
| 52 | 2,4-dichlorophenyl | -n-propyl | H | H | H | H | H | O | Oil |
| 53 | phenyl | -n-propyl | H | CH$_3$ | CH$_3$ | H | H | O | |
| 54 | 4-chlorophenyl | -n-propyl | H | CH$_3$ | CH$_3$ | H | H | O | |
| 55 | 4-fluorophenyl | -n-propyl | H | CH$_3$ | CH$_3$ | H | H | O | |
| 56 | 2,4-dichlorophenyl | -n-propyl | H | CH$_3$ | CH$_3$ | H | H | O | |

*Nitrate salt of compound number 43

| | | | | | | | | | |
|---|---|---|---|---|---|---|---|---|---|
| 57 | 4-chlorophenyl | ethyl | H | -n-C$_3$H$_7$ | H | H | H | O | Gum |
| 58 | 4-chlorophenyl | ethyl | H | -n-C$_3$H$_7$ | H | H | H | O | 110-113 |
| 59 | 4-methylphenyl | ethyl | H | -n-C$_3$H$_7$ | H | H | H | O | Gum |
| 60 | 4-methylphenyl | ethyl | H | -n-C$_3$H$_7$ | H | H | H | O | 117-119 |
| 61 | 4-phenylphenyl | ethyl | H | -n-C$_3$H$_7$ | H | H | H | O | Gum |
| 62 | 4-phenylphenyl | ethyl | H | -n-C$_3$H$_7$ | H | H | H | O | 133-134 |
| 63 | 4-fluorophenyl | ethyl | H | -n-C$_3$H$_7$ | H | H | H | O | Gum |
| 64 | 4-fluorophenyl | ethyl | H | -n-C$_3$H$_7$ | H | H | H | O | 88-90 |
| 65 | 4-methoxyphenyl | ethyl | H | -n-C$_3$H$_7$ | H | H | H | O | Gum |
| 66 | 4-methoxyphenyl | ethyl | H | -n-C$_3$H$_7$ | H | H | H | O | 70-71 |
| 67 | 2,4-dichlorophenyl | ethyl | H | -n-C$_3$H$_7$ | H | H | H | O | |
| 68 | 2,4-dichlorophenyl | ethyl | H | -n-C$_3$H$_7$ | H | H | H | O | |
| 69 | 2-chloro-4-methylphenyl | ethyl | H | -n-C$_3$H$_7$ | H | H | H | O | |
| 70 | 2-chloro-4-methylphenyl | ethyl | H | -n-C$_3$H$_7$ | H | H | H | O | |
| 71 | 4-chlorophenyl | methyl | H | -n-C$_3$H$_7$ | H | H | H | O | |
| 72 | 4-chlorophenyl | methyl | H | -n-C$_3$H$_7$ | H | H | H | O | |
| 73 | 4-methylphenyl | methyl | H | -n-C$_3$H$_7$ | H | H | H | O | |
| 74 | 4-methylphenyl | methyl | H | -n-C$_3$H$_7$ | H | H | H | O | |

TABLE I-continued

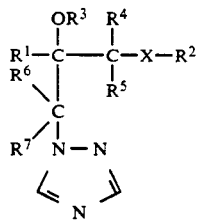

| COMPOUND NO | R¹ | R² | R³ | R⁴ | R⁵ | R⁶ | R⁷ | X | Melting Point °C. |
|---|---|---|---|---|---|---|---|---|---|
| 75 | 4-phenylphenyl | methyl | H | -n-C₃H₇ | H | H | H | O | |
| 76 | 4-phenylphenyl | methyl | H | -n-C₃H₇ | H | H | H | O | |
| 77 | 4-fluorophenyl | methyl | H | -n-C₃H₇ | H | H | H | O | |
| 78 | 4-fluorophenyl | methyl | H | -n-C₃H₇ | H | H | H | O | |
| 79 | 4-methoxyphenyl | methyl | H | -n-C₃H₇ | H | H | H | O | |
| 80 | 4-methoxyphenyl | methyl | H | -n-C₃H₇ | H | H | H | O | |
| 81 | 2,4-dichlorophenyl | methyl | H | -n-C₃H₇ | H | H | H | O | |
| 82 | 2,4-dichlorophenyl | methyl | H | -n-C₃H₇ | H | H | H | O | |
| 83 | 2-chloro-4-methylphenyl | methyl | H | -n-C₃H₇ | H | H | H | O | |
| 84 | 2-chloro-4-methylphenyl | methyl | H | -n-C₃H₇ | H | H | H | O | |
| 85 | phenyl | ethyl | H | allyl | H | H | H | O | |
| 86 | phenyl | ethyl | H | allyl | H | H | H | O | |
| 87 | 4-chlorophenyl | ethyl | H | allyl | H | H | H | O | |
| 88 | 4-chlorophenyl | ethyl | H | allyl | H | H | H | O | |
| 89 | 2,4-dichlorophenyl | ethyl | H | allyl | H | H | H | O | |
| 90 | 2,4-dichlorophenyl | ethyl | H | allyl | H | H | H | O | |

{ signifies diastereoisomer pairs

| | | | | | | | | | |
|---|---|---|---|---|---|---|---|---|---|
| 91 | 4-chlorophenyl | ethyl | H | CH₃ | CH₃ | H | H | O | 90 |
| 92 | 4-fluorophenyl | ethyl | H | CH₃ | CH₃ | H | H | O | 61-63 |
| 93 | 2,4-dichlorophenyl | ethyl | H | CH₃ | CH₃ | H | H | O | |
| 94 | 3-chlorophenyl | ethyl | H | CH₃ | CH₃ | H | H | O | |
| 95 | 3-fluorophenyl | ethyl | H | CH₃ | CH₃ | H | H | O | |
| 96 | t-butyl | ethyl | H | CH₃ | CH₃ | H | H | O | |
| 97 | 4-fluorophenyl | methyl | H | CH₃ | CH₃ | H | H | O | |
| 98 | 2,4-dichlorophenyl | methyl | H | CH₃ | CH₃ | H | H | O | |
| 99 | 3-chlorophenyl | methyl | H | CH₃ | CH₃ | H | H | O | |
| 100 | 3-fluorophenyl | methyl | H | CH₃ | CH₃ | H | H | O | |
| 101 | 4-chlorophenyl | methyl | H | CH₃ | CH₃ | H | H | O | |
| 102 | 4-chlorophenyl | ethyl | H | H | H | H | H | O | 93-94 |
| 103 | 4-fluorophenyl | ethyl | H | H | H | H | H | O | 69-70 |
| 104 | 2,4-dichlorophenyl | ethyl | H | H | H | H | H | O | 75-77 |
| 105 | 3-fluorophenyl | ethyl | H | H | H | H | H | O | |
| 106 | 3-chlorophenyl | ethyl | H | H | H | H | H | O | |
| 107 | t-butyl | ethyl | H | H | H | H | H | O | |
| 108 | 4-chlorophenyl | -n-butyl | H | H | H | H | H | O | |
| 109 | 4-fluorophenyl | -n-butyl | H | H | H | H | H | O | |
| 110 | 2,4-dichlorophenyl | -n-butyl | H | H | H | H | H | O | |
| 111 | t-butyl | -n-butyl | H | H | H | H | H | O | |
| 112 | -n-butyl | 2-pyridyl | H | H | H | H | H | O | |
| 113 | -n-butyl | 6-chloro-2-pyridyl | H | H | H | H | H | O | |
| 114 | t-butyl | 4-phenylbenzyl | H | CH₃ | CH₃ | H | H | O | |
| 115 | t-butyl | 4-phenylbenzyl | H | H | H | H | H | O | |
| 116 | 4-chlorophenyl | 4-phenylbenzyl | H | H | H | H | H | O | |
| 117 | 4-chlorophenyl | 1-methyl-4-isopropyl-cyclohex-3-yl | H | H | H | H | H | O | 84-85* |
| 118 | 4-chlorophenyl | t-butyl | H | H | H | H | H | O | |
| 119 | 4-fluorophenyl | t-butyl | H | H | H | H | H | O | |
| 120 | 2,4-dichlorophenyl | t-butyl | H | H | H | H | H | O | |

TABLE I-continued

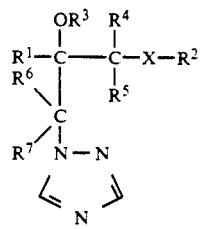

| COMPOUND NO | R¹ | R² | R³ | R⁴ | R⁵ | R⁶ | R⁷ | X | Melting Point °C. |
|---|---|---|---|---|---|---|---|---|---|
| 121 | t-butyl | t-butyl | | H | H | H | H | H | O | |

*derived from l-menthol

The compounds of the invention having the general formula I wherein $R^1$, $R^2$, $R^3$, $R^4$, $R^5$, $R^6$, $R^7$, X and Az are as defined above can be made by treating the epoxides of general formula (II)

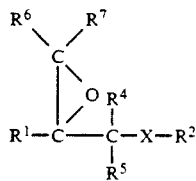 (II)

with 1,2,4-triazole or imidazole either in the presence of an acid-binding agent or in the form of one of its alkali metal salts in a convenient solvent; and, thereafter, oxidising those compounds wherein X=S to obtain those compounds wherein X is SO or SO₂. A suitable oxidising agent is m-chloroperbenzoic acid and the oxidation process is by normal such procedures. In the main process suitably a compound of general formula (II) is reacted at 20°-100° with the sodium or potassium salt of 1,2,4-triazole or imidazole (the salt can be prepared by adding either sodium hydride, a sodium alkoxide or potassium t-butoxide to 1,2,4-triazole or imidazole) in a convenient solvent such as acetonitrile, methanol, ethanol or dimethylformamide. The product can be isolated by pouring the reaction mixture into water and extraction into a suitable solvent.

The epoxides of general formula (II) wherein $R^6=R^7=$hydrogen are made by reacting a ketone of general formula (III)

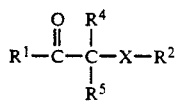 (III)

with dimethyl oxosulphonium methylide (Corey and Chaykovsky, J. Amer. Chem. Soc. 1965, 87, 1353-1364) or dimethyl sulphonium methylide (Corey and Chaykovsky, J. Amer. Chem. Soc. 1962, 84, 3782) using methods set out in the literature. The epoxides of general formula (II) may also be made by the epoxidation of an olefin of general formula (IV)

 (IV)

with the standard oxidising agents such as hypochlorous acid, hydrogen peroxide or peracids (e.g. peracetic or perbenzoic acid). The olefin (IV) is made by treating the ketone of general formula (III) with a Grignard reagent (V)

 (V)

where Y is halogen, for example, chlorine, bromine or iodine, in a convenient solvent such as ether, tetrahydrofuran or anisole and dehydrating the intermediate alcohol. The ketones of general formula (III) may be made by a variety of methods many of which are well known in the literature.

(a) Alkylation of the corresponding α-hydroxy ketones as in Houben Weyl 7/2e p.2232. The α-hydroxy ketones are made by literature methods-Houben Weyl 7/2e pp. 2173-2242.

(b) Grignard reaction of $R^1MgY$ on the appropriate nitrile, $R^2XCR^4R^5CN$, as in Organic Syntheses Collective Volume 3, pp 562-563.

(c) Grignard reaction of $R^1MgY$ on the appropriate acid chloride, $R^2XCR^4R^5COCl$, as in Fumie Sato et al., Tet. Letters, 1979, 44, pp. 4303-4306.

(d) Grignard reaction of $R^1MgY$ on the appropriate aldehyde, $R^2XCR^4R^5CHO$, to give the secondary alcohol followed by oxidation to give the ketone.

(e) Treatment of the epoxide

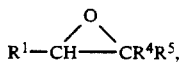

or the halohydrin $R^1$—CHOHCYR⁴R⁵, with $R^2X^\ominus$ as in W. S. Emerson, J. Amer. Chem. Soc. 1945, 69, 516-518 followed by oxidation as in A. Kaelin Helv. Chim. Acta, 1947, 30, 2132-41 to give the ketone.

(f) Reaction of the α-halo ketone

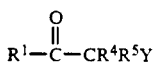

with R²X⁻.

(g) Treatment of the halo-ketal

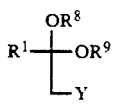

wherein R⁸ and R⁹ are alkyl or together form a ring with RX⁻ followed by acid hydrolysis.

(h) The ketones where R¹ is alkyl or aralkyl can also be made by alkylating the acetylenic alcohol

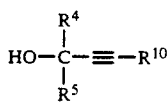

wherein $R^{10}$=H, alkyl, or aryl, followed by hydrolysis as in B D Tiffinay et al., J. Amer. Chem. Soc., 1957, 79, 1682–7.

(i) The ketones where R¹=aryl can be made by Friedel-Crafts reaction between a substituted benzene and the acid chloride

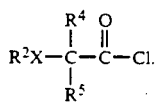

The compounds (I) of the invention can also be prepared by treating the epoxide of general formula (VI)

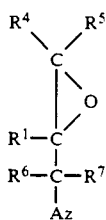     (VI)

with the alkali metal salt of an oxygen or sulphur nucleophile (VII)

$R^2-X^\ominus M^\oplus$     (VII)

in a convenient solvent such as dimethyl formamide and dimethyl sulphoxide at temperatures of 20°–100°. The epoxides of general formula (VI) wherein R⁴=R⁵=H can be prepared by reacting a ketone of general formula (VIII)

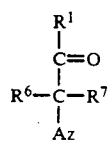     (VIII)

with dimethyl oxosulphonium methylide (Corey and Chaykovsky, J. Amer. Chem. Soc. 1965, 87, 1353–1364) or dimethyl sulphonium methylide (Corey and Chaykovsky, J. Amer. Chem. Soc. 1962, 84, 3782) using methods set out in the literature.

The ketones of general formula (VIII) can be made by methods set out in the patent literature (British Patents Nos. 1533705/6).

The salts and metal complexes of the compounds of general formula (I) can be prepared from the latter in known manner. For example, the complexes can be made by reacting the uncomplexed compound with a metal salt in a suitable solvent.

The compounds, salts and metal complexes are active fungicides, particularly against the diseases:

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants *Plasmopara viticola* on vines *Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines Helminthosporium spp. and Rhynchosporium spp. on cereals *Cercospora arachidicola* on peanuts and other Cercospora species on for example sugar beet, bananas and soya beans *Botrytis cinerea* (grey mould) on tomatoes, strawberries, vines and other hosts *Venturia inaequalis* (scab) on apples Some of the compounds have also shown a broad range of activities against fungi in vitro. They have activity against various post-harvest diseases on fruit (e.g. *Penicillium digatatum* and italicum on oranges and *Gloeosporium musarum* on bananas). Further some of the compounds are active as seed dressings against: Fusarium spp., Septoria spp., Tilletia spp. (i.e. bunt, a seed borne disease of wheat), Ustilago spp., Helminthosporium spp. on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

The compounds, and their derivatives as defined above, also have plant growth regulating activities.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals and soya bean where reduction in stem growth may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerate*, Festuca spp. (e.g. *Festuca rubra*) and Poa spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape fruit trees (e.g. apples). Some coniferous trees are not significantly stunted by the compounds so the compounds could be useful in controlling undesirable vegetation in conifer nurseries.

The plant growth regulating effect may (as implied) above) manifest itself in an increase in crop yield.

In the potato, vine control in the field and inhibition of sprouting in the store may be possible.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. In grass swards an increase in tillering could lead to a denser sward which may result in increased resilience in wear.

The treatment of plants with the compounds can lead to the leaves developing a darker green colour.

The compounds may inhibit, or at least delay, the flowering of sugar beet and thereby may increase sugar yield. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds are also useful for the treatment of candidiasis and human dermatophyte infections.

The compounds may be used as such for fungicidal or plant growth regulating purposes but are more conveniently formulated into compositions for such usage. The invention thus provides also a fungicidal composition comprising a compound of general formula (I) or a salt or complex thereof as hereinbefore defined, and a carrier or diluent.

The invention also provides a method of combating fungal diseases in a plant, which method comprises applying to the plant, to seed of the plant, or to the locus of the plant or seed, a compound, or a salt or complex thereof, as hereinbefore defined.

The invention further provides a method of combating fungal diseases in a plant, which method comprises applying to the plant, to seed of the plant or to the locus of the plant or seed, a compound, or a salt or complex thereof, as hereinbefore defined.

The compounds, salts and complexes can be applied in a number of ways, for example they can be formulated or unformulated, directly to the foliage of a plant, to seeds or to other medium in which plants are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein include seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient(s). These concentrates suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal activity or compounds having plant growth regulating, herbicidal or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazitine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenapanil, ofurace, propiconazole, etaconazole and fenpropemorph.

The compounds of general formula (I) can be mixed with soil, peat or other rooting media for the protection of plants against seed-borne, soil-borne or foliar fungal diseases.

Suitable insecticides are Pirimor, Croneton, dimethoate, Metasystox and formothion.

The other plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides.

Examples of suitable plant growth regulating compounds are the gibberellins (e.g. $GA_3$, $GA_4$ or $GA_7$, the auxins (e.g. indoleacetic acid, indole-butyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or NCPA), substituted benzoic acids (e.g. triiodobenzoic acid), morphactins (e.g. chlorfluorecol), maleic hydrazide, glyphosate, glyphosine, long chain fatty alcohols and acids, dikegulac, fluoridamid, mefluidide, substituted quaternary ammonium and phosphonium compounds (e.g. chlormequat or chlorphonium), ethephon, carbetamide, methyl-3,6-dichloranisate, daminozide, asulam, abscissic acid, isopyrimol, 1(4-chlorophenyl)-4,6-dimethyl-2-oxo-1,2-dihydropyridine-3-carboxylic acid, hydroxybenzonitriles (e.g. bromoxynil), difenzoquat, benzoylpropethyl, and 3,6-dichloropicolinic acid.

The following Example illustrates the invention; the temperatures are given in degrees Centigrade (°C.).

EXAMPLE 1

This Example illustrates the preparation of 3,3-dimethyl-1-(4-chlorophenoxy)-2-(1,2,4-triazol-1-ylmethyl)butan-2-ol (Compound No. 1 of Table I).

Stage I

To a solution of dimsyl sodium, prepared by reacting sodium hydride (1.1 parts) with dimethyl sulphoxide (40 ml) under nitrogen atmosphere at 60°-70°, was added with cooling, trimethylsulphonium iodide (9.42 parts) dissolved in dimethyl sulphoxide (40 ml), over a period of 5 minutes. After stirring for an additional five minutes, α-4-chlorophenoxy pinacolone (10 parts) dissolved in tetrahydrofuran (80 ml) was added rapidly and kept at 0° for about 10 minutes. The cooling bath was removed and the stirring was continued for another hour. The reaction mixture was then poured into water (300 ml) and the aqueous solution was extracted three times with petroleum ether (30°-40°). The combined organic extract was washed with water, dried ($K_2CO_3$) and the solvent was removed to obtain the oxirane.

Stage II

To a suspension of potassium tertiary-butoxide (1.9 parts) in dimethylformamide (30 ml) was added 1,2,4-triazole (1.15 parts) in dimethylformamide (30 ml) dropwise at room temperature and the mixture was kept at 60° for one hour. The solution was cooled to 0° to $-5°$ and the oxirane (4 parts) described in Stage I was dissolved in dimethylformamide (15 ml) and added dropwise with stirring. The reaction mixture was allowed to warm to room temperature and then heated at 50° for three hours.

The mixture was poured into water (200 ml) and any of the unreacted oxirane that was precipitated was filtered off. The filtrate was extracted with ether (50 ml) three times. The combined ether extract was washed with water, dried ($MgSO_4$) and the solvent removed. The yellow residue was purified by flash chromatography over silica gel (230-400 mesh) and eluted with ethyl acetate: petroleum ether (60°-80°) (1:1) to yield the title compound as a white solid, m.p. 85.5°-87°.

EXAMPLE 2

This Example illustrates the preparation of 3,3-dimethyl-1-(4-chlorophenylsulphenyl)-2-(1,2,4-triazol-1-ylmethyl)butan-2-ol (Compound No. 22 of Table I).

Dry dimethylsulphoxide (DMSO: 70 ml) was added dropwise with stirring to a mixture of sodium hydride (1.73 g) and trimethylsulphoxonium iodide (15.80 g) under nitrogen and stirred for 1 hour at room temperature. A solution of α-triazolylpinacolone (10.00 g) in DMSO (30 ml) was added to the resulting ylide solution and stirred for 5 hours at room temperature. The mixture was poured into water and extracted with ether. The combined extracts were washed with water, dried over $MgSO_4$, and concentrated to give a colourless oil (4.51 g) whose infrared spectrum showed no carbonyl absorption.

A solution of the colourless oil (4.51 g) in dry dimethylformamide (DMF: 10 ml) was added with stirring to a solution of sodium 4-chlorothiophenoxide [from sodium hydride (0.65 g) and 4-chlorothiophenol (3.96 g)] in DMF (40 ml) under nitrogen and stirred for 2 hours at room temperature. The mixture was poured into water and extracted with ether. The combined extracts were washed with water, dried over $MgSO_4$, and concentrated to give the title compound (6.58 g, 34% from α-triazolylpinacolone) as a viscous colourless oil which crystallised on standing, m.p. 64°-65°.

EXAMPLE 3

This Example illustrates the preparation of 3,3-dimethyl-1-(4-chlorophenylsulphinyl)-2-(1,2,4-triazol-1-ylmethyl)butan-1-ol (Compound No. 26 of Table I).

m-Chloroperbenzoic acid (1.40 g) was added in portions to a stirred solution of 3,3-dimethyl-1-(4-chlorophenylsulphenyl)-2-(1,2,4-triazol-1-ylmethyl)butan-2-ol (2.12 g) in dichloromethane (100 ml) at 5°. After 0.5 hours the reaction mixture was washed successively with aqueous $NaHCO_3$ and water, dried over $MgSO_4$, and concentrated to give the title compound as a white solid (1.62 g, 73%), m.p. 140°-145° (decomp.).

EXAMPLE 4

This Example illustrates the preparation of 3,3-dimethyl-1-(4-chlorophenylsulphonyl)-2-(1,2,4-triazol-1-ylmethyl)butan-2-ol (Compound No. 31 of Table I).

m-Chloroperbenzoic acid (4.20 g) was added in portions to a stirred solution of 3,3-dimethyl-1-(4-chlorophenylsulphenyl)-2-(1,2,4-triazol-1-ylmethyl)butan-2-ol (3.18 g) in dichloromethane (100 ml) at room temperature. After 1 hour the reaction mixture was washed successively with aqueous $NaHCO_3$ and water, dried over $MgSO_4$, and concentrated to give the title compound as a white solid (2.18 g, 62%), m.p. 114°-116° (decomp.).

This Example illustrates the preparation of 1-(1,2,4-triazol-1-yl)-2-(4-methylphenyl)-3-ethoxyhexan-2-ol (compound nos. 59 and 60 of Table I).

Boron trifluoride etherate (1.8 ml) was added to a stirred mixture of 1,1-diethoxybutane (32.1 g) and trimethylsilyl cyanide (22.0 g) at room temperature: exotherm. After 3 hours, aqueous sodium bicarbonate was added and the mixture was extracted with ether. The extracts were dried over $MgSO_4$ and concentrated to give an orange oil (36.0 g) containing 2-ethoxyvaleronitrile (Compare: K. Utimoto, Y. Wakabayashi, Y. Shishiyama, M. Inoue and H. Nozaki, *Tetrahedron Letters*, 1981, 22, 4279). A solution of part of this crude material (9.0 g) in dry tetrahydrofuran (THF: 20 ml) was added to a stirred solution of 4-methylphenyl magnesium bromide [from 4-bromotoluene (9.4 g) and magnesium (1.98 g)] in dry THF (80 ml) under nitrogen and the resulting mixture was heated under reflux for 3 hours. After cooling, dilute sulphuric acid was added and the mixture was extracted with ether. The combined extracts were washed with water, dried over magnesium sulphate, and concentrated under reduced pressure to give a red oil (10.0 g) which was purified by column chromatography on silica gel using dichloromethane as eluant to give 1-ethoxy-1-(4-methylbenzoyl)butane (5.7 g, 47% from 1,1-diethoxybutane) as an orange oil, IR: 1680 cm$^{-1}$.

A suspension of sodium hydride (0.70 g) in dry dimethylsulphoxide (DMSO: 40 ml) was stirred at 50° under a nitrogen atmosphere for 2.5 hours. The resulting clear solution was diluted with dry THF (40 ml) and cooled in an ice-salt bath. Solutions of trimethylsulphonium iodide (5.9 g) in DMSO (40 ml) and 1-ethoxy-1-(4-methylbenzoyl)butane (5.22 g) in THF (40 ml) were added successively to the stirred dimsyl sodium solution, maintaining the temperature of the reaction mixture at about 0°. After 15 minutes the cooling bath was removed and after a further 1.5 hours the reaction mixture was diluted with water and extracted with ether. The combined extracts were washed with water, dried over magnesium sulphate, and concentrated under reduced pressure to give a mixture of diastereoisomers of 1,2-epoxy-2-(4-methylphenyl)-3-ethoxyhexane (5.15 g, 93%) as a yellow oil.

A solution of 1,2-epoxy-2-(4-methylphenyl)-3-ethoxyhexane (4.7 g) in dry dimethylformamide (DMF: 10 ml) was added to a stirred solution of sodium triazole [from 1,2,4-triazole (2.07 g) and sodium hydride (0.72 g)] in DMF (40 ml) under nitrogen, and the mixture was heated at 50°-60° for 3 hours. Water was added, the mixture was extracted with ether, and the combined extracts was washed with water, dried over magnesium sulphate, and concentrated to give a crude mixture of diastereoisomers of the title compound (5.43 g) as a yellow oil.

Chromatography on a column of silica gel using ether as eluant gave (i) Diastereoisomer A (2.04 g, 34%) as a yellow oil, R$_f$ (Et$_2$O/silica gel) 0.3; (ii) a mixture of diastereoisomers A and B (0.80 g, 13%) as a yellow oil; (iii) diastereoisomer B (0.87 g, 14%) as a white crystalline solid, m.p. 117°-119° C., R$_f$ (Et$_2$O/silica gel) 0.2 (found: C,67.20; H,8.02; N,14.02%. C$_{17}$H$_{25}$N$_3$O$_2$ requires C,67.33; H,8.25; N,13.86%).

EXAMPLE 6

This Example illustrates the preparation of 1-(1,2,4-triazol-1-yl)-2-(4-chlorophenyl)-3-isopropoxy-propan-2-ol (compound no. 42 of Table I)

Stage 1

Metallic sodium (3.0 g atoms, 69 g) was added to isopropyl alcohol (1250 ml) at such a rate so as to maintain gentle reflux. When all the sodium had reacted chloroacetic acid (1.5 mol., 142 g) in isopropyl alcohol (180 ml) was added dropwise maintaining gentle reflux. After the addition the solution was refluxed for a further 4 hours. The isopropyl alcohol was distilled off, the solid residue dissolved in water (500 ml) and the solution cooled in an ice-salt bath. Concentrated HCl (200 ml) was added dropwise, the sodium chloride filtered off and the filtrate saturated with sodium sulphate. The aqueous solution was extracted with diethyl ether (5×250 ml) and the ether removed in vacuo to give an orange liquid which distilled at reduced pressure to give isopropoxy acetic acid (70%), b.p. 98°-100°/ 10 mm Hg.

Stage 2

Isopropoxy acetic acid (0.6 mol, 70.8 g) was added dropwise to thionyl chloride (0.72 mol 86 g), stirred at 60° for 1.5 hours and heated to 100° for half an hour to complete the reaction. Distillation gave isopropoxy acetyl chloride (95%), b.p. 140°-141°.

Stage 3

Isopropoxy acetyl chloride (0.37 mol, 50 g) was added dropwise with caution to 80/80 ammonia (250 ml) cooled in an ice-salt bath keeping the temperature between 10°-15°. After the addition the solution was stirred at room temperature for 6 hours then reduced to dryness in vacuo. The residue was extracted with hot ethyl acetate (3×250 ml) and the solution dried over anhydrous sodium sulphate. Removal of the solvent gave isopropoxyacetoamide (85%) as a white crystalline solid, m.p. 41°-42°.

Stage 4

Isopropoxyacetoamide (0.21 mol, 25 g) and thionyl chloride (0.26 mol, 30 g) were heated under gentle reflux for 1 hour. Distillation at atmospheric pressure gave isopropoxyacetonitrile (40%) as a colourless liquid b.p. 149°-150°.

Stage 5

The Grignard reagent was prepared from 4-chloroiodobenzene (0.066 mol, 15.7 g) and magnesium (0.066 g atoms, 1.6 g) in dry diethyl ether (50 ml). To this ice-cooled solution was added isopropoxyacetonitrile (0.055 mol, 5.5 g) in dry ether (7 ml) and the solution allowed to stand at room temperature for 2 hours. After cooling in an ice-salt bath the complex was decomposed by adding water (80 ml) and dilute H$_2$SO$_4$ (30 ml). The ether solution was washed with dilute H$_2$SO$_4$ (100 ml), water (100 m), saturated sodium bicarbonate solution (100 ml), and dried over anhydrous sodium sulphate. Removal of the ether gave an orange oil which was purified by medium pressure column chromatography (silica Crosfield SD210 eluted with toluene) to give α-isopropoxy-4-chloroacetophenone (40%) as a golden yellow oil.

Stage 6

50% Sodium hydride (0.03 mol, 1.44 g) was washed with petroleum ether, suspended in dry dimethyl sulphoxide (30 ml) and heated at 70° under a nitrogen atmosphere for 2 hours. After cooling to room temperature, dry tetrahydrofuran (30 ml) was added and the solution cooled to 0°. Trimethylsulphonium iodide (0.03 mol, 6.12 g) dissolved in dry dimethyl sulphoxide (30 ml) was added dropwise at 0°, stirred for two minutes, and α-isopropoxy-4-chloroacetophenone (0.015 mol, 3.2 g) in dry dimethyl sulphoxide (15 ml) and dry tetrahydrofuran (15 ml) was added dropwise at 0°. The solution was stirred at room temperature for 4 hours, poured into ice water (200 ml), and extracted with (3×200 ml). The ether solution was washed with water (3×150 ml) and dried over anhydrous sodium sulphate. Removal of the solvent gave 1-(4-chlorophenyl)-1-isopropoxymethyl ethylene oxide (90%) as a pale yellow oil.

Stage 7

50% Sodium hydride (0.02 mol, 0.96 g) was washed with petroleum ether and suspended in dry dimethyl formamide (20 ml). 1,2,4-Triazole (0.02 mol 1.38 g) was added portionwise at room temperature and stirred at room temperature until the effervescence ceased. 1-(4-chlorophenyl)-1-isopropoxymethylethylene oxide (0.01 mol, 2.26 g) in dimethyl formamide (2 ml) was added and the solution stirred at 80° for 5 hours. After cooling to room temperature the solution was poured into water (200 ml), extracted with ether (2×150 ml), washed with water (2×150 ml), and dried over anhydrous sodium sulphate. Removal of the solvent gave a pale yellow oil which was purified by column chromatography (silica Crosfield SD 210 eluted with ethyl acetate) to give the title compound (70%) as an oil.

EXAMPLE 7

The compounds were tested against a variety of foliar fungal diseases of plants. The technique employed was as follows.

The plants were grown in John Innes Potting Compost (No 1 or 2) in 4 cm diameter minipots. A layer of fine sand was placed at the bottom of the pots containing the dicotyledonous plants to facilitate uptake of test compound by the roots. The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on *Botrytis cinerea*, *Plasmopara viticola* and *Venturia inaequalis*. The sprays were applied to maximum retention and the root drenches to a final concentration equivalent to approximately 40 ppm a.i./dry soil. Tween 20, to give final concentration of 0.05%, was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:

4 = no disease
3 = trace-5% of disease on untreated plants
2 = 6-25% of disease on untreated plants
1 = 26-59% of disease on untreated plants
0 = 60-100% of disease on untreated plants The results are shown in Table II.

TABLE II

| COMPOUND NUMBER | PUCCINIA RECONDITA (WHEAT) | ERYSIPHE GRAMINIS (BARLEY) | PLASMOPARA VITICOLA (VINE) | BOTRYTIS CINEREA (GRAPE OR TOMATO) | CERCOSPORA ARACHIDICOLA (PEANUT) | VENTURIA INAEQUALIS (APPLE) |
|---|---|---|---|---|---|---|
| 1 | 4 | 4 | 0 | 4 | 4 | 4 |
| 2 | 4 | 4 | 0 | — | 4 | 4 |
| 4 | 4 | 4 | 1 | 0 | 4 | 4 |
| 7 | 4 | 4 | 1 | 0 | 4 | 3 |
| 10 | 4 | 4 | 3 | 0 | 3 | 4 |
| 12 | 4 | 4 | 0 | 0 | 0 | 0 |
| 13 | 4 | 4 | 0 | — | 4 | 4 |
| 14 | 4 | 4 | 4 | 0 | 4 | 4 |
| 15 | 4 | 4 | 0 | — | 3 | 3 |
| 16 | 0 | 4 | 0 | — | 2 | 3 |
| 17 | 4 | 4 | 3 | 0 | 4 | 4 |
| 18 | 4 | 4 | 1 | 0 | 4 | 4 |
| 19 | 4 | 4 | 0 | 0 | 4 | 4 |
| 20 | 4 | 4 | 2 | 0 | 4 | 4 |
| 21 | 4 | 4 | 1 | 0 | 4 | 4 |
| 22 | 4 | 4 | 0 | 3 | 4 | 4 |
| 23 | 0 | 4 | 2 | — | 2 | 0 |
| 24 | 4 | 4 | 0 | 0 | 3 | 4 |
| 25 | 4 | 4 | 0 | 0 | 4 | 2 |
| 26 | 4 | 4 | 0 | 0 | 4 | 3 |
| 27 | 1 | 4 | 0 | — | 2 | 3 |
| 28 | 4 | 4 | 0 | 0 | 4 | 4 |
| 29 | 4 | 4 | 1 | 0 | 4 | 2 |
| 30 | 4 | 4 | 0 | 0 | 3 | 0 |
| 31 | 4 | 4 | 0 | 0 | 4 | 4 |
| 32 | 4 | 4 | 2 | 4 | 4 | 4 |
| 33 | 3 | 4 | 1 | 0 | 3 | 4 |
| 34 | 4 | 4 | — | 0 | 4 | 4 |
| 35 | 4 | 4 | 0 | 0 | 4 | 4 |
| 36 | 4 | 4 | 0 | 0 | 4 | 4 |
| 37 | 4 | 4 | 0 | 0 | 4 | 4 |
| 38 | 4 | 4 | 0 | 0 | 4 | 4 |
| 39 | 4 | 4 | 0 | 0 | 4 | 4 |
| 40 | | | | | | |
| 41 | | | | | | |
| 42 | | | | | | |
| 57 | | | | | | |
| 58 | | | | | | |
| 59 | | | | | | |

TABLE II-continued

| COMPOUND NUMBER | PUCCINIA RECONDITA (WHEAT) | ERYSIPHE GRAMINIS (BARLEY) | PLASMOPARA VITICOLA (VINE) | BOTRYTIS CINEREA (GRAPE OR TOMATO) | CERCOSPORA ARACHIDICOLA (PEANUT) | VENTURIA INAEQUALIS (APPLE) |
|---|---|---|---|---|---|---|
| 60 | | | | | | |

EXAMPLE 8

This Example illustrates the plant growth regulating properties of the compounds. The compounds were applied as an overall spray of an emulsifiable concentrate diluted to give the concentrations shown in Table III. The plants were grown in 3" pots in peat compost and sprayed at the 2 leaf stage. Plant growth regulating effects were assessed 12 days after application of the compounds. Retardation of growth was scored on a 0–3 scale where:

1 = 0–30% retardation
2 = 31–75% retardation
3 = 75% retardation

Additional plant growth regulating properties are indicated as follows:
G = darker green leaf colour
A = apical effect
T = tillering effect The results are shown in Table III. If no figure is given the compound was substantially inactive as a stunting agent.

TABLE III

| COMPOUND | DAT | RATE (ppm) | AT | CC | DA | LT | SB | TO | SY | CT | MZ | WW | BR |
|---|---|---|---|---|---|---|---|---|---|---|---|---|---|
| 2 | 12 | 4000 | | | | 2 | 1 | 1 | | 1 | | | |
| 4 | 12 | 2000 | 3 | 3 | 3 | 3 | 2G | 3G | 3GT | | 2 | 2T | T |
| 13 | 12 | 4000 | 3G | 2 | 2G | 3GA | 3G | 2GT | 2G | 3G | 3G | 3GT | 2 |
| | 12 | 2000 | 3 | 3G | 2 | 3 | 3G | 3G | 3GT | 2G | 3 | 3T | 2T |
| | 12 | 1000 | 3 | 3 | 3 | 3G | 3G | 3G | 3GT | 1G | 1 | 3 | 1T |
| | 12 | 400 | 2 | 3 | 2 | 3 | 2 | 2G | 3GT | G | 1 | 3T | 1T |
| | 12 | 100 | 3 | 3 | 2 | 3 | 1 | 1G | 2T | | G | 3T | T |
| 15 | 12 | 4000 | | | 1 | 2 | 1 | 1 | | 2 | | T | |

Key to test species in Table III
AT *Agrostis tenuis*
CC *Cynosurus cristatus*
DA *Dactylis glomerata*
LT *Lactaca sativa*
SB *Beta vulgaris*
TO *Lycopersicon esculentum*
SY *Glycine max*
CT *Gossypium hirsutum*
MZ *Zea mays*
WW *Triticum aestivum*
BR *Hordeum vulgare*

EXAMPLE 9

An emulsifiable concentrate was made up by mixing the ingredients, and stirring the mixture until all the constituents were dissolved.

| Compound of Example 1 | 10% |
|---|---|
| Ethylene dichloride | 40% |
| Calcium dodecylbenzenesulphate | 5% |
| "Lubrol" L | 10% |
| "Aromasol" H | 35% |

EXAMPLE 10

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.

| Compound of Example 1 | 50% |
|---|---|
| "Dispersol" T | 25% |
| "Lubrol" APN5 | 1.5% |
| Sodium acetate | 23.5% |

EXAMPLE 11

The ingredients were all ground together to produce a powder formulation readily dispersible in liquids.

| Compound of Example 3 | 45% |
|---|---|
| "Dispersol" T | 5% |
| "Lissapol" NX | 0.5% |
| "Cellofas" B600 | 2% |
| Sodium acetate | 47.5% |

EXAMPLE 12

The active ingredient was dissolved in a solvent and the resultant liquid was sprayed on to the granules of China clay. The solvent was then allowed to evaporate to produce a granular composition.

| Compound of Example 4 | 5% |
|---|---|
| China clay granules | 95% |

EXAMPLE 13

A composition suitable for use as a seed dressing was prepared by mixing the three ingredients.

| Compound of Example 5 | 50% |
|---|---|
| Mineral oil | 2% |

-continued

| | |
|---|---|
| China clay | 48% |

EXAMPLE 14

A dusting powder was prepared by mixing the active ingredient with talc.

| | |
|---|---|
| Compound of Example 6 | 5% |
| Talc | 95% |

EXAMPLE 15

A Col formulation was prepared by ball-milling the constituents set out below and then forming an aqueous suspension of the ground mixture with water.

| | |
|---|---|
| Compound of Example 1 | 40% |
| "Dispersol" T | 10% |
| "Lubrol" APN5 | 1% |
| Water | |

EXAMPLE 16

A dispersible powder formulation was made by mixing together the ingredients set out below and then grinding the mixture until all were thoroughly mixed.

| | |
|---|---|
| Compound of Example 2 | 25% |
| "Aerosol" OT/B | 2% |
| "Dispersol" A.C. | 5% |
| China clay | 28% |
| Silica | 40% |

EXAMPLE 17

This Example illustrates the preparation of a dispersible powder formulation. The ingredients were mixed and the mixture then ground in a comminution mill.

| | |
|---|---|
| Compound of Example 3 | 25% |
| "Perminal" BX | 1% |
| "Dispersol" T | 5% |
| Polyvinylpyrrolidone | 10% |
| Silica | 25% |
| China clay | 34% |

EXAMPLE 18

The ingredients set out below were formulated into a dispersible powder by mixing then grinding the ingredients.

| | |
|---|---|
| Compound of Example 4 | 25% |
| "Aerosol" OT/B | 2% |
| "Dispersol" A | 5% |
| China clay | 68% |

In Examples 9 to 18 the proportions of the ingredients given are by weight. The remaining compounds of Table I were similarly formulated.

There now follows an explanation of the compositions or substances represented by the various Trade Marks and Trade Names mentioned above.

LUBROL L: a condensate of nonyl phenol 1 mole) with ethylene oxide (13 moles)

AROMASOL H: a solvent mixture of alkylbenzenes

DISPERSOL T & AC: a mixture of sodium sulphate and a condensate of formaldehyde with sodium naphthalene sulphonate LUBROL APN5: a condensate of nonyl phenol (1 mole) with naphthalene oxide (5.5 moles)

CELLOFAS B600: a sodium carboxymethyl cellulose thickener

LISSAPOL NX: a condensate of nonyl phenol (1 mole) with ethylene oxide (8 moles)

AEROSOL OT/B: dioctyl sodium sulphosuccinate

PERMINAL BX: a sodium alkyl naphthalene sulphonate

We claim:

1. A triazole compound having the formula (I):

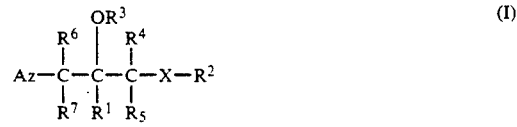

wherein $R^1$ is halophenyl and $R^2$ is hydrogen, $C_1-C_6$ alkyl or phenyl substituted with halogen; $R^3$ is hydrogen; $R^4$ and $R^5$, which may be the same or different, are hydrogen or $C_1-C_6$ alkyl; $R^6$ and $R^7$ are hydrogen; X is SO or $SO_2$; and Az is a 1,2,4- or 1,3,4-triazole ring; and isomers, acid addition salts and metal complexes thereof.

2. A method of combating fungal diseases in a plant which comprises applying to the plant or the locus of the plant, an effective amount of a compound as claimed in claim 1.

* * * * *